United States Patent [19]

Halikas

[11] Patent Number: 5,102,913

[45] Date of Patent: Apr. 7, 1992

[54] TREATMENT FOR COCAINE USE EMPLOYING VALPROIC ACID

[76] Inventor: James A. Halikas, 22 Hill Farm Cir., North Oaks, Minn. 55127

[21] Appl. No.: 724,105

[22] Filed: Jul. 1, 1991

[51] Int. Cl.$^5$ ............................................. A61K 31/19
[52] U.S. Cl. .................................... 514/557; 514/812
[58] Field of Search ................................. 514/557, 812

[56] References Cited

U.S. PATENT DOCUMENTS 4,942,182  7/1990  Weiss et al. ........................... 514/812
5,028,611  7/1991  Halikas ................................. 514/277

OTHER PUBLICATIONS

Halikas et al., "Carbamazepine for Cocaine Addiction?", The Lancet, Mar. 18, 1989, pp. 623-624.
Dackis et al., Arch. Gen. Psychiatry, 44:298-299, 1987.
Dackis and Gold, "Pharmacological Approaches to Cocaine", J. Subst. Abuse Treat., 2:139-145 (1985).
Post et al., "The Role of Context and Conditioning in Behavioral Sensitization to Cocaine", Pharm. Bulletin, vol. 23, No. 3, pp. 425-429 (1987).
Post et al., "Kindling and Drug Sensitization: implications for the progressive development of psychopathology and treatment with carbamazepine", The Psychopharmacology of Anticonvulsants, pp. 27-53 (1981).
Post, "Time Course of Clinical Effects of Carbamazepine: Implications for Mechanisms of Action", J. Clin. Psychiatry, 49:4(Suppl), Apr. 1988, pp. 35-46.
Post et al. in "Differential Effects of Carbamazepine and Lithium on Sensitization and Kindling", Prog. Neuro-Psychopharmacol & Biol Psychiat., 1984, vol. 8, pp. 425-434.
Ballenger et al., "Kindling as a Model for Alcohol Withdrawal Syndromes", Brit. J. Psychiat., (1978), 133, 1-14.
Post et al., "Conditioning, Sensitization, and Kindling: Implications for the Course of Affective Illness," Chapter 28, pp. 432-466 of Neuro. Bio. of Mood Disorders, (1984).
"Tegretol Said to Be Valuable Drug in Treatment of Benzodiazepine Withdrawal", Psychiatric News, May 5, 1989.
Article from Minneapolis Star/Tribune, Sep. 12, 1989 entitled, "Cure for Craving? Psychiatrist thinks he has found pill to battle cocaine".
Ballenger et al., "Neurobiological Correlates of Depression and Anxiety in Normal Individuals", Date and Publication not available, chapter 30, pp. 481-501.
"Winning the Drug War One Battle at a Time", University of Minnesota Medical Bulletin, Summer 1990 p. 6.
"Dr. James Halikas Finds That A Pill Made for Seizures May Help Cocaine Addicts To Just Say No", People Weekly, 33:3 p. 81 (1990).
Gawin and Ellinwood, "Cocaine and Other Stimulants: Actions, Abuse and Treatment", New England Journal of Medicine, 318:18 p. 1173 (1988).
Giannini and Billett, "Bromocriptine-Desipramine Protocol in Treatment of Cocaine Addiction", J. Clin. Pharmacol 1987; 27:549-554.
Post and Weiss, "Sensitization, Kindling, and Anticonvulsants in Mania", J. Clin. Psychiatry 50:12 (Suppl.) Dec. 1989.
Perez-Reyes et al, "Free-base Cocaine Smoking", Clin. Pharmacol. Ther., Oct. 1982, p. 459.
Tennant et al, "Double-Blind Comparison of Desipramine and Placebo for Treatment of Phencyclidine or Amphetamine Dependence".
Kleber and Gawin, "Psychopharmacological Trials in Cocaine Abuse Treatment", Am. J. Drug Alcohol Abuse 12(3) pp. 235-246 (1986).
Cocores et al, "Cocaine Abuse and Adult Attention Deficit Disorder", J. Clin. Psychiatry 48:9, p. 376, Sep. 1987.
Resnick and Resnick, "Cocaine Abuse and its Treatment", Psychiatric Clinics of North America, 7:4, p. 713, Dec. 1984.
Kleber, "Introduction: Cocaine Abuse: Historical, Epidemiological, and Psychological Perspectives", J. Clin. Psychiatry 49:2, p. 3 (Suppl) Feb. 1988.
Fischman, "Behavioral Pharmacology of Cocaine", J. Clin. Psychiatry 49:2, p. 7 (Suppl) Feb. 1988.
Gawin, "Chronic Neuropharmacology of Cocaine: Progress in Pharmacotherapy", J. Clin. Psychiatry 49:2 p. 11 (Suppl) Feb. 1988.
O'Brien et al., "Pharmacological and Behavioral Treatments of Cocaine Dependence: Controlled Studies", J. Clin. Psychiatry 49:2, 17 (Suppl) Feb. 1988.
Baxter, Jr. et al, "Localization of Neurochemical Effects of Cocaine and Other Stimulants in the Human Brain", J. Clin. Psychiatry 49:2 p. 23 (Suppl) Feb. 1988.
Millman, "Evaluation and Clinical Management of Cocaine Abusers", J. Clin. Psychiatry 49:2 p. 27 (Suppl) Feb. 1988.
Blumer et al., "Indications for Carbamazepine in Mental Illness: Atypical Psychiatric Disorder or Temporal Lobe Syndrome?", Comprehensive Psychiatry, 29:2, pp. 108-122 (1988).
Price et al., "Management of Acute PCP Intoxication with Verapamil", Clinical Toxicology, 24(1), 85-87 (1986).
Karler et al., "Blockade of 'Reverse Tolerance' to Cocaine and Amphetamine by MK-801", Life Sciences, 45:599-606 (1989).

(List continued on next page.)

[57] ABSTRACT

The craving for cocaine and use of cocaine among users may be reduced by administration of valproic acid. Cocaine-usage is effectively treated with valproic acid administration.

7 Claims, No Drawings

OTHER PUBLICATIONS

Scher and Neppe, "Carbamazepine Adjunct for Nonresponsive Psychosis with Prior Hallucinogenic Abuse", Journal of Nervous and Mental Disease, 177:12, p. 755 (1989).

Brown et al., "Alcohol Detoxification and Withdrawal Seizures: Clinical Support for a Kindling Hypothesis", Biol Psychiatry 23:507–514 (1988).

Smith, David E., "Diagnostic, Treatment and Aftercare Approaches to Cocaine Abuse", from Journal of Substance Abuse Treatment, vol. 1 pp. 5–9, 1984.

Nursing 89 Drug Handbook, Springhouse Corp., Springhouse, PA (1989) pp. 264, 280.

Nahas, G. et al., Bull Acad Natl Med 173(9):1199–1206, 12/89 (Abstract).

Gale, K., NIDA Res Monogr Ser 54:323–332, 1984 (Abstract).

Post, R. M. et al., Neuro-Psychopharmacol Biol Psychiatr 7(2–3);263–271, 1983.

*Primary Examiner*—Frederick E. Waddell
*Assistant Examiner*—Diane Gardner
*Attorney, Agent, or Firm*—Vidas & Arrett

TREATMENT FOR COCAINE USE EMPLOYING VALPROIC ACID

BACKGROUND OF THE INVENTION

1. Field of the Invention

This invention relates to a method for reducing the use of cocaine in animals, including humans, by the administration of valproic acid.

2. Description of the Related Art

Treatment for cocaine abuse has been largely ineffective, based on cocaine relapse rates. Depending on the level of habituation or dependence, and prognostic features, i.e. job, marital status, additional psychopathology, etc., upwards of 60-100% of cocaine dependent patients relapse within the first 12 months no matter how high their motivation. For most, this relapse rate is due to an overwhelming "craving" for the drug (Dackis et al, *Arch. Gen. Psychiatry*, 44: 298-9, 1987).

There have been a number of studies in which various pharmacologic agents have been used to treat cocaine dependence: Bromocriptine, bromocriptine-desipramine combination, amantadine, imipramine, L. L.tyrosine and L.tryptophan in combination, and desipramine. Both amantadine and bromocriptine have been used primarily to treat the cocaine withdrawal syndrome but long-term studies using either have not yet been conducted.

The tricyclic antidepressant, desipramine, has been the most extensively studied of pharmacologic agents. Maintenance with desipramine for 3-4 weeks is required before any significant decrease in craving occurs.

Biological hypotheses regarding cocaine craving have focused on the dopaminergic reward pathways. Two of the more recent theories have suggested that craving is at least in part due to a "down" regulation of the dopamine reward system following chronic cocaine abuse. Instead, the inventor postulates that cocaine craving involves an alternate specific neurophysiological mechanism related to kindling.

The inventor filed U.S. patent application Ser. No. 07/373,385, filed June 25, 1989, on a method for treating cocaine use with carbamazepine. That application is to issue on July 2, 1991 as U.S. Pat. No. 5,028,611, the disclosure of which is incorporated herein by reference. Further papers concerning the use of carbamazepine by the inventor include Halikas et al, "Carbamazepine for Cocaine Addiction?", *The Lancet*, Mar. 18, 1989, pp. 623-624; Halikas et al, "Reduction of Cocaine Use Among Methadone Maintenance Patients Using Concurrent Carbamazepine Maintenance", *Annals of Clinical Psychiatry*, 1990, 2: 3-6; and Halikas et al, "A Possible Neurophysiological Basis of Cocaine Craving", *Annals of Clinical Psychiatry*, 1990, 2: 79-83.

U.S. Pat. No. 4,942,182 to Post et al, which issused July 17, 1990, involves blocking "toxic effects" and "reinforcing effects" of cocaine in rats using carbamazepine. Post has also published an article in *The Journal of Clinical Psychiatry*, "Introduction: Emerging Perspectives on Valproate in Affective Disorders" (1989); 50(3)(Sec. 2): 3-9.

The art described in this section is not intended to constitute an admission that any patent, publication or other information referred to herein is "prior art" with respect to this invention, unless specifically designated as such. In addition, this section should not be constructed to mean that a search has been made or that no other pertinent information as defined in 37 C.F.R. §1.56(a) exists.

SUMMARY OF THE INVENTION

It has been found that daily administration of valproic acid will decrease the "craving" for cocaine. It is the craving which makes the habit so difficult to break. Valproic acid is an anticonvulsant that has been used effectively to control seizure disorder.

A cocaine abuser was treated with valproic acid in a dose of 250 mg per day increased to a maximum of 1500 mg per day. The craving for cocaine and cocaine dreams were effectively controlled. Psychostimulants and psychoactive drugs also cause kindling, the facilitation of neuronal activity. Therefore, valproic acid may be used to treat abuse of such drugs. Valproic acid, also known as valproate sodium, is an effective drug to diminish cocaine craving in humans or other drug related cravings involving kindling.

DESCRIPTION OF THE PREFERRED EMBODIMENTS

Cocaine Craving

Cocaine craving is a subjective psychological state characterized by an overwhelming urge or compulsion to repeat the drug experience. Intravenous cocaine users describe a profound loss of control, and will frequently self-administer single bolus doses every 10-20 minutes until access to the drug is no longer available. Craving which occurs several weeks into the recovery process can also be extremely intense. This delayed craving seems related to a memory "replay" of the original drug experience, elicited by environmental cues which have become associated with cocaine use. These triggers are endlessly diverse and highly individualized.

The term "kindling" in neurophysiology refers to the progressive facilitation of neuronal firing, in discrete regions of the brain, elicited by temporally spaced exposure to specific pharmacologic or electrical stimuli. When induced pharmacologically, this neuronal firing occurs with progressively lower doses of stimuli. In animals, this firing can increase in magnitude to seizure activity. Tatum and Seevers, *J. Pharmacal. Exp. Ther.*, 36: 401-410, (1929), over fifty years ago, observed that giving rats, dogs and monkeys the same dose of cocaine, produced increasing psychomotor excitability and eventual lethality. Goddard et al, *Exp. Neurol.* 25: 295 (1969), demonstrated the electrical kindling phenomenon by delivering fixed daily amounts of electrical stimulation to the region of the amygdala in rats. Previously non-convulsant test animals eventually developed seizures, with a permanent lowering of the seizure threshold.

More recently, pharmacologic kindling has been extensively investigated by Post and Kopanda, *Am. J. Psychiatry*, 133: 627-734 (1976), using a variety of psychomotor stimulants and anesthetics. Temporally spaced injections, more than 24 hours apart of fixed subconvulsive doses of cocaine, elicited major motor seizures as an endpoint in the kindling process, with a variety of mid-stage kindling "behavioral" responses.

Ellinwood and Kilbey *Animal Model in Psychiatry & Neurology*, Ed: E. Hanin & E. Usdin, N.Y. (1977), observed mid-stage kindling or "behavioral sensitization" effects of repeated administration of amphetamine, which was labeled reverse tolerance. Animals of all species studies developed specific stereotypy and disruption of learned behavior (mid-stage), before they progressed to major motor seizures (late stage).

In animals, limbic system structures, especially the amygdala and hippocampus, produce prominent seizure and after-discharge activity in response to cocaine administration in adequate doses. This electrical activity may then spread outside the limbic system and be associated with major motor seizures. It should be noted that the hippocampus has been shown to have an "exceedingly low" threshold for seizure activity and to be involved in learning and memory processes.

Post, Kopanda, and Black, *Bio. Psychiatry*, 11: 403-419 (1976), demonstrated, in rhesus monkeys, that an individual standard sub-seizure-threshold dose of cocaine, when administered repeatedly over time, intraperitoneally, resulted in the onset of seizures. Once a seizure had been produced, the average number of cocaine doses required to produce a seizure decreased with time. In one of their animals, a single cocaine dose was eventually needed to induce seizure activity.

It has been suggested that in humans the progressive increases in irritability, restlessness, hypervigilance and paranoia associated with chronic high-dose cocaine use may be the human correlate of the kindling phenomenon in the animal research paradigm.

Pollock, *Pyschiat. J. Univ. of Ottawa* 10: 4, 185-192 (1985), has summarized the major characteristics of the kindling process. First, the progressive lowering of after-discharge threshold in surrounding neuronal tissue occurs in response to stimuli of physiologic proportion. The kindling response is enhanced when the interval between stimuli is 24 hours or greater. If stimuli are less than two hours apart kindling is significantly delayed. Secondly, Pollock suggests that kindling progresses through stages which can be observed and recorded prior to late-stage kindling which is major motor seizure activity. Specific behavior changes, such as stereotypy, and EEG changes correspond to the stepwise progression of mid-stage kindling. A third feature of kindling pertains to gradients of neural susceptibility. Certain areas of the brain, amygdala and limbic system structure are much more sensitive to the kindling phenomenon than are the neocortex, brain stem and cerebellum which are relatively impervious to kindling. A fourth aspect of kindling is related to its sustained effect. Kindled animals appear to have permanent neuronal sensitivity, which is not explained on the basis of toxic metabolites, pharmacokinetic factors or destructive lesions at the tip of the electrode.

In the dopamine system, cocaine causes decreased release of dopamine from the ventro-medial mesencephalon, inhibited uptake of dopamine in mesoaccumbens neurons, increased dopamine metabolism in the striatum, and possibly induces dopamine autoreceptor supersensitivity.

Cocaine affects the norepinephrine system by inhibiting the spontaneous firing of locus ceruleus neurons, increasing hypothalamic metabolism, and decreasing norepinephrine synthesis. The serotonin system is affected by inhibited synaptosomal uptake of serotonin, decreased-serotonin concentration in the caudate, decreased serotonin turnover in the brain, and reduced serotonin synthesis (reflected by decreased uptake of tryptophan and decreased tryptophan hydroxylase activity.

Cocaine-induced, or "kindled", seizures have been documented in animals. A search of the scientific literature has not yielded any reports as yet of human cocaine-kindled seizures. In the course of treatment of cocaine addicts at the University of Minnesota Hospitals, a human example of cocaine-kindled seizures was encountered.

Testing

Case Report: Human Cocaine-Kindled Seizure Activity

The patient is a 38-year old white male with a lengthy history of cocaine dependence and also opioid dependence for which he is on methadone maintenance. The patient has no history of cranial trauma or personal or family history of seizure disorder or other neurologic disorder. For the past 20 years, except for a two-year prison-induced abstinence, the patient has regularly, but intermittently, used cocaine, almost exclusively by the intravenous (IV) route. He has used up to 5 grams per day. Prior to 1984, the patient had never experienced any seizures while administering intravenous cocaine to himself. In 1984, the patient experienced a seizure-like episode after having used a total of 4-5 grams of cocaine intravenously in 0.2-0.3 gram boluses within a 12-hour period. This seizure episode consisted of clonic activity of both upper extremities and "staring straight ahead. I just couldn't do anything about it," which lasted for an estimated 2-3 minutes without loss of consciousness or sphincter incontinence. Prior to this episode, the first 0.2-0.3 grams of cocaine taken during a session would produce euphoria. This seizure episode greatly disturbed the patient but he found himself essentially powerless in the face of his cocaine dependence.

During the next 12 months the patient discovered that he would experience seizure activity of this type after using a total of 3-4 grams of cocaine over the course of a day. The seizures would frighten him, and he would cease cocaine use. The next morning he would feel compelled by his dependence to use again. A bolus of approximately 0.2 grams of cocaine at that time would, within approximately 30 seconds, produce another seizure episode, this time accompanied by the instant paranoid feeling of having been discovered by law enforcement authorities, and by auditory hallucination, consisting of non-threatening voices. He frequently noticed himself drooling following these seizure episodes. He once waited approximately three days following an IV cocaine-induced seizure episode prior to using cocaine again and still precipitated a seizure on his first injection of an approximately 0.2-0.3 gram bolus.

During the next 2-3 years the patient discovered that it took progressively less total grams of IV cocaine to precipitate a seizure of the type indicated above. In recent months a total of only 0.5 grams could produce a seizure. The extent, character, and magnitude of the seizure has not changed over time, but the patient is unsure whether the duration of each seizure episode has increased.

Since August, 1988, as part of an open label treatment protocol, the patient has received carbamazepine as adjunctive therapy for his cocaine dependence. Although he has taken the medication intermittently, he has had only six days' of cocaine use in 14 weeks. When he takes the carbamazepine, he reports significantly reduced craving. Without the carbamazepine, he reports a return of severe craving for cocaine. Five of the days of cocaine use occurred when he had stopped taking the carbamazepine for several days. The other single day of cocaine use occurred while he was taking carbamazepine.

Over the course of one week, the patient had, without the knowledge or approval of his physician, increased his carbamazepine dose to 900 mg per day. He then used a total of about 3 grams of cocaine IV over a six-hour period in 0.2–0.3 gram boluses. He experienced euphoria, but only after he has used 0.5 grams total over about one-half hour. He denied experiencing a seizure, but did finally experience paranoia after he has used a total of about 1.5 grams over 2–3 hours.

An MRI scan of the patient's brain was negative for any pathology. A sleep-deprived EEG, done while the patient was not taking carbamazepine, demonstrated intermittent right temporal lobe focal slowing.

This man has developed cocaine-induced clonic seizures and they have become progressively more easily initiated at lower and lower cocaine doses because of putative development and spread of "kindling".

Kindling Hypothesis of Cocaine Craving

Valproic acid blocks early development of pharmacologically-induced kindling and cocaine kindled seizure activity. There appear to be several "behavioral" manifestations of developing kindling in animals short of major motor seizures already identified, including sterotypy, disrupted learning, and reverse tolerance. In humans, too, there may be many manifestations of developing kindling. It is hypothesized on the basis of clinical observations of reduction of craving in this population that cocaine craving may be the psychological and behavioral manifestation of the kindling or neuronal supersensitivity seen in animal studies. It is hypothesized that the changes brought about by cocaine in the limbic system, specifically the kindling noted in the amygdala and the hippocampus, and the decreased firing rate of locus ceruleus neurons, is also present in humans, although this has not as yet been demonstrated. It is contended that this kindling in humans is the basis of the behavior which is termed "craving." This cocaine craving is reduced or reversed at both a neurophysiological level and at a behavioral level with valproic acid. The behavioral conditioning principles of intermittent reinforcement and imprinting may be related to these same neurophysiological events. In cocaine dependent patients, long-term or delayed craving for cocaine may be the behavioral manifestation of kindling. This is named the Kindling Hypothesis of Cocaine Craving.

Other Psychostimulants and Psychoactive Compounds

In addition to cocaine, over the last 60 years, the kindling phenomenon in animals has been documented with a variety of other psychostimulants, amphetamines, local anesthetics, and electrical stimulation. Although comparable work has not yet been done with phencyclidine (PCP) or lysergic acid diethylamide (LSD), it is a reasonable extension of kindling hypothesis to expect that they also will cause facilitation of neuronal activity. This would account for the clinical observation in the 1960's and 1970's of "flashbacks" with LSD, and the observation in the 1970's and 1980's of residual mental changes of a semi-permanent nature in patients who had abused PCP repeatedly. Other drugs which have either been demonstrated to cause kindling, or could be expected to cause kindling based on this hypothesis, include:

Methamphetamine
Methylene dioxymethamphetamine (MDMA)
Amphetamine
D amphetamine
Methylphenidate
DL phenylpropanolamine (PPA)
Procaine
Lidocaine
Methedrine
Desoxyn
Cocaine
Freebase
Crack On the basis of the consistency of the hypothesis and clinical observations to date, it is expected that valproic acid will provide an effective treatment to reduce or eliminate the use of psychostimulants and psychoactive agents as well as cocaine.

Kindling Related Disorders

It has been demonstrated that animal and human behavior can be taught with relatively few trails if the organism is ready for the new experience, and trained at the right moment in its growth and development. In behavioral psychology this type of learning is called "imprinting". In humans, there has long been a clinical observation that certain traumatic psychological or physical events may leave a lasting, recurrent upsetting memory. While this has been most obvious with Vietnam veterans, it is also seen with adults who have been physically or sexually abused in childhood. This has now been labeled, clinically, the Post-Traumatic Stress Disorder (PTSD). Some patients with this syndrome have recurring patterns of dreams and nightmares, violent outbursts in response to unpredicted environmental triggers, and a high propensity to alcohol abuse and depression. There is at least one clinical study indicating that carbamazepine is useful in alleviating the symptoms of Post-Traumatic Stress Disorder. This would be consistent with the hypothesis regarding the development of kindling in these patients. In this case, not on the basis of an external chemical introduced into the creature, but rather on the basis of a sudden, excessive, emotionally traumatic sensory overload which is imprinted electrically in the same areas of the limbic system as are other forms of kindling. In short, a plausible extension of the hypothesis is that traumatic events may cause the development of a similar facilitation of neutral activity which could be treated with valproic acid.

Valproic Acid

Valproic acid, valproate sodium and divalproex sodium are carboxylic acid-derivative anticonvulsants. Valproate sodium is rapidly converted to valproic acid in the stomach. Divalproex sodium dissociates into valproate. Valproic acid is structurally unrelated to other commercially available anticonvulsants.

During a double-blind study a crack cocaine user being treated with carbamazepine was given divalproex sodium. The patient had not responded well to carbamazepine but wanted to diminish his craving for cocaine. He was begun on Depakote brand divalproex sodium from Abbott Laboratories with weekly 250 mg increases through the first four weeks. At week six he was stabilized at 1250 mg per day. Medication was removed at the end of week nine, when dosage was 1500 mg per day.

He had spent about $2000 monthly on crack cocaine. After three days of medication with divalproex sodium he stopped using cocaine and was able to work regularly without problems and his marital strife disappeared. Cocaine craving and cocaine-use dreams had been eliminated.

It is believed that the minimum therapeutic level should be similar to that based on seizure disorder patients. Thus, one would expect that adults would respond well to a dosage of about 1200 to 1500 mg of valproic acid per day. Initially, dosage of between about 100 to 350 mg should be administered daily, with weekly increases until the craving appears to be controlled. The dosage may vary with age, body weight and severity of craving. The onset of therapeutic effects is several days to a week.

When used herein, "valproic acid" shall refer to valproic acid, valproate sodium, divalproex sodium and any other drug that will be seen as valproic acid in the body. It may be administered orally and in other forms useful in seizure disorder therapy. Rectal and intragastric administration has been effective for seizure disorder syndrome.

While this invention may be embodied in many different forms, there are shown in the drawings and described in detail herein specific preferred embodiments of the invention. The present disclosure is an exemplification of the principles of the invention and is not intended to limit the invention to the particular embodiments illustrated.

This completes the description of the preferred and alternate embodiments of the invention. Those skilled in the art may recognize other equivalents to the specific embodiment described herein which equivalents are intended to be encompassed by the claims attached hereto.

What is claimed is:

1. A method for reducing the use of psychostimulants and psychoactive compounds which cause kindling in animals, which method comprises administering to an animal in need an effective amount of valproic acid or a pharmaceutically acceptable acid addition salt thereof.

2. The method of claim 1 wherein said psychostimulants and psychoactive compounds are selected from the group consisting of phencyclidine (PCP), lysergic acid diethylamide (LSD), methamphetamine, methylene dioxymethamphetamine (MDMA), amphetamine, D amphetamine, methylphenidate, DL phenylpropanolamine (PPA), Procaine, Lidocaine, Methedrine, Desoxyn, cocaine, freebase and Crack.

3. A method for treating drug abuse in patients taking a drug which causes pharmacologically-induced kindling, which method comprises administering to a patient in need an effective amount of valproic acid or a pharmaceutically acceptable acid addition salt thereof.

4. A method for reducing the craving for cocaine in living animals in need thereof which method comprises administering thereto an effective amount of valproic acid or a pharmaceutically acceptable acid addition salt thereof.

5. A method for reducing the craving for cocaine in humans in need thereof which method includes the step of orally administering daily thereto between about 1200 to about 1500 mg valproic acid or a pharmaceutically acceptable acid addition salt thereof.

6. The method of claim 5 wherein said human is initially given valproic acid or a pharmaceutically acceptable acid addition salt thereof in a 100 to 350 mg dosage which progressively increases until craving is eliminated to a maximum of about 1500 mg per day.

7. A method for treating cocaine addiction in man by reducing the craving for cocaine, the method including the step of ingesting valproic acid or a pharmaceutically acceptable acid addition salt thereof in an initial 250 mg dosage followed by progressive increases until cocaine use is controlled, up to a maximum of about 1500 mg per day.

* * * * *